US008285369B2

(12) United States Patent
Kuo et al.

(10) Patent No.: US 8,285,369 B2
(45) Date of Patent: Oct. 9, 2012

(54) METHOD FOR DELINEATION OF CHARACTERISTIC POINTS IN AN ELECTROCARDIOGRAM SIGNAL, AND STORAGE MEDIUM, ELECTRONIC DEVICE AND ELECTROCARDIOGRAM SIGNAL ANALYZING SYSTEM FOR IMPLEMENTING THE METHOD

(75) Inventors: Cheng-Deng Kuo, Taipei (TW); Po-Ching Chen, Taipei (TW); Steven Lee, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 1441 days.

(21) Appl. No.: 11/807,800

(22) Filed: May 30, 2007

(65) Prior Publication Data

US 2008/0300496 A1 Dec. 4, 2008

(51) Int. Cl.
*A61B 5/04* (2006.01)
(52) U.S. Cl. ......... 600/509; 600/508; 600/515; 600/517
(58) Field of Classification Search .................. 600/508, 600/509, 515, 517
See application file for complete search history.

(56) References Cited

U.S. PATENT DOCUMENTS

2006/0111642 A1* 5/2006 Baura et al. ................... 600/513

OTHER PUBLICATIONS

Yu-Ping Wang; et al., "Chromosome image enhancement using multiscale differential operators," IEEE Transactions on Medical Imaging, vol. 22, No. 5, pp. 685-693, May 2003.*
Chen, Po-Ching, et al. "Delineation of T-Wave in ECG by Wavelet Transform Using Multiscale Differential Operator." IEEE Transactions on Biomedical Engineering (2006) vol. 53, No. 5 pp. 1429-1433.
Zhang, Kai, et al., Abstract of "Wavelet transform method for automatic detection of electrocardiogram signals", *Journal of Yangzhou University, Natural Science Edition*, 2001-4(1), 1 page.
Wu, S-chien, "Wavelet-Transform-Based 12 Lead ECG Characteristic-Points Extraction", *Master Thesis of Chung Hua University*, Sep. 2006, 69 pages.

* cited by examiner

*Primary Examiner* — Niketa Patel
*Assistant Examiner* — Lindsey G. Hankins
(74) *Attorney, Agent, or Firm* — Ladas & Parry LLP (57) ABSTRACT

A method for delineation of characteristic points in an electrocardiogram signal includes the steps of: (a) processing the electrocardiogram signal to obtain at least one multiscale differential operator wavelet transform thereof; and (b) locating at least one characteristic point in at least one wave segment of the electrocardiogram signal based on the at least one multiscale differential operator wavelet transform.

15 Claims, 7 Drawing Sheets

METHOD FOR DELINEATION OF CHARACTERISTIC POINTS IN AN ELECTROCARDIOGRAM SIGNAL, AND STORAGE MEDIUM, ELECTRONIC DEVICE AND ELECTROCARDIOGRAM SIGNAL ANALYZING SYSTEM FOR IMPLEMENTING THE METHOD

BACKGROUND OF THE INVENTION

1. Field of the Invention

The invention relates to a method for delineation of an electrocardiogram signal, more particularly to a method for delineation of characteristic points in an electrocardiogram signal, and a storage medium, an electronic device, and an electrocardiogram signal analyzing system for implementing the method.

2. Description of the Related Art

Figure 1:
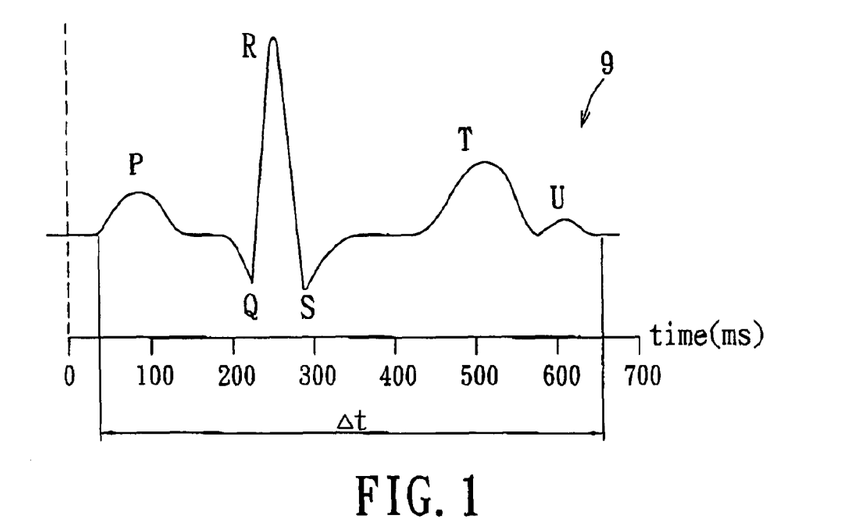
FIG. 1 is a plot of an illustrative electrocardiogram signal to show different wave segments thereof.

As shown in FIG. 1, an electrocardiogram (ECG) signal 9 can be divided into a P-wave, a Q-wave, an R-wave, a T-wave and a U-wave for every period ($\Delta t$) of the electrocardiogram signal 9. In terms of diagnostic and biological significance, the PR interval between the P-wave and the R-wave represents the time during contraction of the atria and the ventricles; the QRS-interval of a QRS-complex between the Q-wave and the S-wave represents the time during transmission of electricity from the AV node to the ventricles for causing the ventricles to contract; and the QT interval between the Q-wave and the T-wave represents the time during recovery of the ventricles after contraction occurs. Therefore, how to accurately and effectively delineate and locate the various wave segments and intervals in an electrocardiogram signal is crucial to making correct diagnoses.

In clinical diagnoses, doctors usually locate the wave intervals in an electrocardiogram signal by naked eye observation based on grids provided on a record graph paper. As technology advances, several delineation methods for electrocardiogram signals have been developed and implemented in computer-executable manners. For instance, Barro et al. developed a diagnostic system based on the method of spectral analysis for detection of severe pathological changes such as ventricular tachycardia and ventricular fibrillation. In the diagnostic system, diseases are indicated by corresponding spectral characteristic distributions of the electrocardiogram signal, and the spectral characteristic distributions are taken as the basis for diagnostic reading of the electrocardiogram signal. Murthy et al. implemented the method of spectral analysis to characterize the P-wave, QRS-complex and T-wave in an electrocardiogram signal based on the spectral differences among the various waves. Woolfsion et al. used the method of zero-crossing to analyze life threatening cardiac arrhythmia, and compared various characteristics of the method of zero-crossing and the method of spectral analysis. Okada et al. used a simple combination of digital filters for the detection of the QRS-complex and for the measurement of the interval of the QRS-complex. Hamilton et al. used digital filtering techniques for quantitative investigation of the QRS-complex detection. Atarius et al. used the method of maximum likelihood for detection of the phenomenon of cardiac late potentials when the heart suffers from myocardial ischemia or myocardial anoxia.

In addition, S. Mallat et al. applied the method of multiscale differential operator (MDO) for edge detection in image processing. However, the applicants are unaware of a teaching in the prior art to apply the method of multiscale differential operator to the delineation of electrocardiogram signals and the categorization of wave segment morphologies.

Although the abovementioned methods are capable of delineating certain wave segments in an electrocardiogram signal, such as the obvious QRS-complex, precise locations of on and off points of each wave segment, especially the T-wave, cannot be determined using the same methods. This is because the T-wave is a more complex wave segment, starts more gradually, and has a lot of varying shapes as compared to the R-wave or other wave segments in an electrocardiogram signal.

SUMMARY OF THE INVENTION

Therefore, the object of the present invention is to provide a method for delineation of various wave segments of an electrocardiogram signal that is capable of locating on, off and peak points of the T-wave with accuracy.

According to one aspect of the present invention, there is provided a method for delineation of characteristic points in an electrocardiogram signal. The method includes the steps of:

(a) processing the electrocardiogram signal to obtain at least one multiscale differential operator wavelet transform thereof; and (b) locating at least one characteristic point in at least one wave segment of the electrocardiogram signal based on the at least one multiscale differential operator wavelet transform.

According to another aspect of the present invention, there is provided a computer-readable storage medium comprising program instructions for causing a computing apparatus to execute consecutive steps of a method for delineation of characteristic points in an electrocardiogram signal. The method includes the steps of:

(a) receiving an electrocardiogram signal;

(b) processing the electrocardiogram signal to obtain at least one multiscale differential operator wavelet transform thereof; and (c) locating at least one characteristic point in at least one wave segment of the electrocardiogram signal based on the at least one multiscale differential operator wavelet transform.

According to yet another aspect of the present invention, there is provided an electronic device comprising program instructions for causing the electronic device to execute consecutive steps of the method for delineation of characteristic points in an electrocardiogram signal.

According to still another aspect of the present invention, there is provided an electronic device capable of delineating characteristic points in an electrocardiogram signal that includes: means for receiving an electrocardiogram signal; means for processing the electrocardiogram signal to obtain at least one multiscale differential operator wavelet transform thereof; and means for locating at least one characteristic point in at least one wave segment of the electrocardiogram signal based on the at least one multiscale differential operator wavelet transform.

According to a further aspect of the present invention, an electrocardiogram signal analyzing system includes an analog-to-digital converting unit and a signal processing unit. The analog-to-digital converting unit converts an analog electrocardiogram signal into a corresponding digital electrocardiogram signal. The signal processing unit is coupled electrically to the analog-to-digital converting unit, and includes a storage medium and a digital signal processor. The storage medium is receiving and storing the digital electrocardiogram signal, and has an electrocardiogram point delineation program stored therein. The digital signal processor is coupled electrically to the storage medium for retrieving the electrocardiogram point delineation program, and performs consecutive steps of a method for delineation of characteristic points in the digital electrocardiogram signal through execution of the electrocardiogram point delineation program. The method includes: (a) processing the digital electrocardiogram signal to obtain at least one multiscale differential operator wavelet transform thereof; and (b) locating at least one characteristic point in at least one wave segment of the electrocardiogram signal based on the at least one multiscale differential operator wavelet transform.

BRIEF DESCRIPTION OF THE DRAWINGS

Other features and advantages of the present invention will become apparent in the following detailed description of the preferred embodiment with reference to the accompanying drawings, of which:

FIG. 6(*a*) are plots to illustrate a first standard electrocardiogram signal $f_1(t)$, and barriers, turning points and fade-away points located for a T-wave segment through first to third order multiscale differential operator wavelet transforms obtained for the first standard electrocardiogram signal according to the method of the present invention;

FIG. 6(*b*) are plots to illustrate a second standard electrocardiogram signal $f_2(t)$ with a negative T-wave segment categorized into a first category according to the method of the present invention;

FIG. 6(*c*) are plots to illustrate a third standard electrocardiogram signal $f_3(t)$ with an ascending T-wave segment categorized into a second category according to the method of the present invention;

FIG. 6(*d*) are plots to illustrate a fourth standard electrocardiogram signal $f_4(t)$ with a descending T-wave segment categorized into the second category according to the method of the present invention; and FIG. 6(*e*) are plots to illustrate a fifth standard electrocardiogram signal $f_5(t)$ with a biphasic T-wave segment categorized into a third category according to the method of the present invention.

DETAILED DESCRIPTION OF THE PREFERRED EMBODIMENT

Before the present invention is described in detail in terms of the preferred embodiment, the principal concept and formulas will be explained first.

1. Wavelet Transform

Wavelet transform is a numerical analysis capable of multi-resolution analysis, and is therefore widely used in signal analysis. During signal transformation and encoding, a signal is projected on to a basic function, and the coefficient corresponding to the basic function is the encoded portion of the signal. An efficient encoding method is to concentrate the signal energy onto a small number of coefficients during signal transformation, and wavelet transform provides this characteristic.

In the present invention, a translation (u) and a scale (s) of a mother wavelet function $\psi(t)$ are used to decompose an original signal f(t) into a plurality of elementary elements. The wavelet transform $W_s f(u)$ of the original signal f(t) is defined in Equation 1 as follows.

$$W_s f(u) = \int_{-\infty}^{+\infty} f(t) \frac{1}{\sqrt{s}} \psi^*\left(\frac{t-u}{s}\right) dt = f \otimes \overline{\psi}_s(u) \qquad \text{Equation 1}$$

where * denotes complex conjugate, and $\hat{x}$ denotes convolution, and where the function $\overline{\psi}_s(t)$ is defined in Equation 2 as follows.

$$\overline{\psi}_s(t) = \frac{1}{\sqrt{s}} \psi^*\left(\frac{-t}{s}\right) \qquad \text{Equation 2}$$

2. Modulus Maxima

Assume that a modulus maximum of the wavelet transform $W_s f(u)$ of the original signal f(t) is used to describe any point $(u_0, s_0)$, such that the absolute value $|W_{s_0} f(u)|$ of the wavelet transform $W_{s_0} f(u)$ having $s=s_0$ substituted into Equation 1 is locally maximum at $u=u_0$. This relationship is defined in Equation 3 as follows.

$$\left. \frac{\partial W_{s_0} f(u)}{\partial u} \right|_{u=u_0} = 0 \qquad \text{Equation 3}$$

When the wavelet transform $W_s f(u)$ of the original signal f(t) is at fine scale, Equation 3 can be used to find the point of convergence of the wavelet transform $W_s f(u)$. In other words, through differentiation of the wavelet transform $W_s f(u)$ using Equation 3, the abscissa of the modulus maximum of the wavelet transform $W_s f(u)$ can be determined.

3. Multiscale Differential Operator

Multiscale differential operator is mainly used in magnifying characteristic points of a signal. Through integration of wavelet transform and multiscale differential operator, marker points of the T-wave and other wave segments of an electrocardiogram signal can be defined accurately.

Assume that there exists a function $\theta(t)$ with a fast decay. Given that the function $\theta(t)$ is a Gaussian smoothing function, the mother wavelet function $\psi(t)$ can be written in Equation 4 as follows.

$$\psi(t) = (-1)^n \frac{d^n \theta(t)}{dt^n} \qquad \text{Equation 4}$$

where n=1 denotes a first order differentiation, n=2 denotes a second order differentiation, and n=3 denotes a third order differentiation.

In order to understand the properties of the modulus maxima of the original signal f(t), the wavelet transform $W_s f(u)$ is written as a multiscale differential operator wavelet transform $W_s^n f(u)$ as provided below in Equation 5, where the mother wavelet function $\psi(t)$ for the multiscale differential operator wavelet transform $W_s^n f(u)$ is defined in Equation 4 with varying values of n. In other words, Equation 1 can be rewritten as Equation 5.

$$W_s^n f(u) = s^n \frac{d^n}{du^n}(f \otimes \overline{\theta}_s)(u) \quad \text{Equation 5}$$

$$\text{where } \overline{\theta}_s(t) = s^{\frac{-1}{2}} \theta^* \left(\frac{-t}{s}\right) \quad \text{Equation 6}$$

In Equation 5, the first order multiscale differential operator wavelet transform is denoted by $W_s^1 f(u)$ with n=1, the second order multiscale differential operator wavelet transform is denoted by $W_s^2 f(u)$ with n=2, and the third order multiscale differential operator wavelet transform is denoted by $W_s^3 f(u)$ with n=3.

The zero-crossing of the first order multiscale differential operator wavelet transform $W_s^1 f(u)$ defines a peak of the original signal f(t).

The first and last modulus maxima of the second order multiscale differential operator wavelet transform $W_s^2 f(u)$ define turning points of the original signal f(t).

The first and last modulus maxima of the third order multiscale differential operator wavelet transform $W_s^3 f(u)$ define fade-away points of the original signal f(t).

Figure 2:
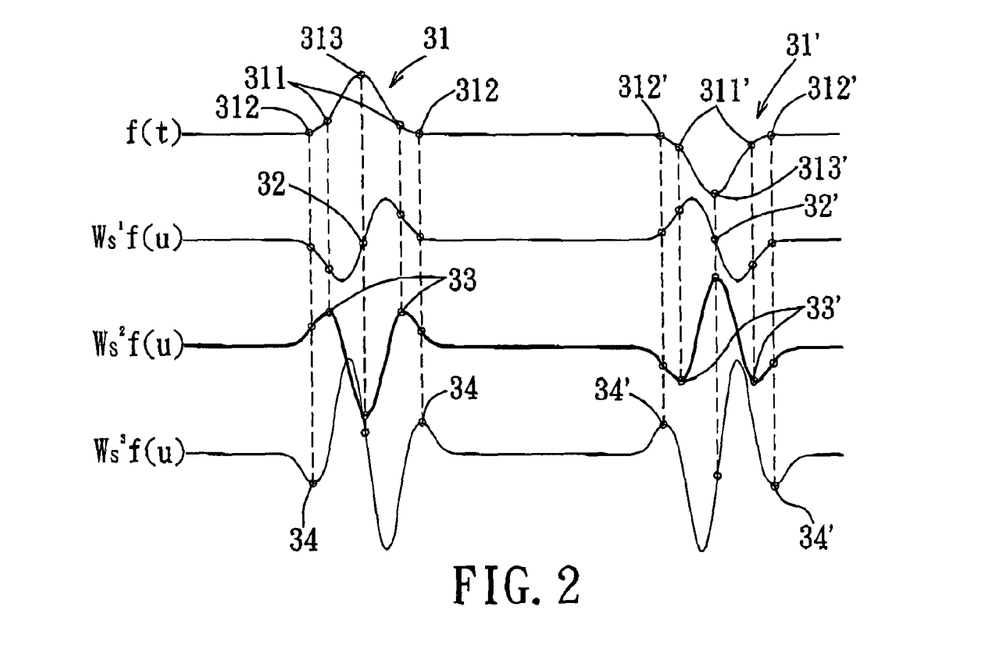
FIG. 2 are plots to illustrate an exemplary electrocardiogram signal f(t), and first to third order multiscale differential operator wavelet transforms obtained for the exemplary electrocardiogram signal according to the method of the present invention.

Shown in FIG. 2 is an exemplary electrocardiogram signal f(t) for the purpose of illustration, where a first wave segment 31 of the exemplary electrocardiogram signal f(t) has two turning points 311, two fade-away points 312, and a peak point 313, and a second wave segment 31' of the exemplary electrocardiogram signal f(t) has two turning points 311', two fade-away points 312', and a peak point 313'.

Figure 3:
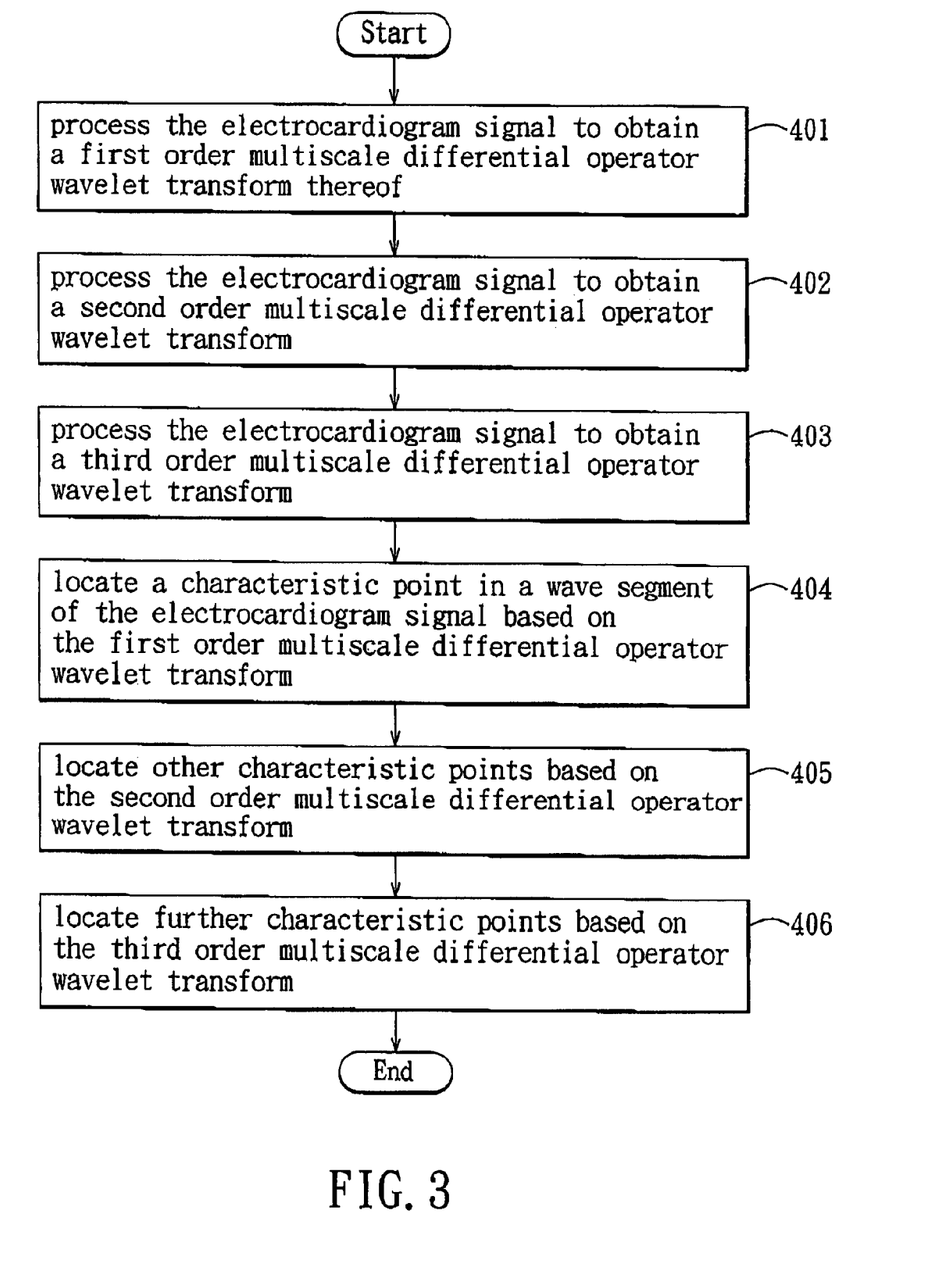
FIG. 3 is a flowchart of the preferred embodiment of the method for delineation of characteristic points in an electrocardiogram signal according to this invention.

With further reference to FIG. 3, applying the method for delineation of characteristic points in an electrocardiogram signal according to the preferred embodiment of the present invention, the exemplary electrocardiogram signal f(t) is first processed to obtain a first order multiscale differential operator wavelet transform $W_s^1 f(u)$ thereof (step 401). Then, the exemplary electrocardiogram signal f(t) is processed to obtain a second order multiscale differential operator wavelet transform $W_s^2 f(u)$ (step 402). Subsequently, the exemplary electrocardiogram signal f(t) is processed to obtain a third order multiscale differential operator wavelet transform $W_s^3 f(u)$ (step 403). Next, based on the first order multiscale differential operator wavelet transform $W_s^1 f(u)$, at least one characteristic point in at least one wave segment of the exemplary electrocardiogram signal f(t) is located (step 404). In particular, a zero-crossing 32 of the first order multiscale differential operator wavelet transform $W_s^1 f(u)$ defines the maximum extremity of the first wave segment 31 of the exemplary electrocardiogram signal f(t), i.e., the peak 313. Another zero-crossing 32' of the first order multiscale differential operator wavelet transform $W_s^1 f(u)$ defines the minimum extremity of the second wave segment 31' of the exemplary electrocardiogram signal f(t), i.e., the peak 313'. Similarly, based on the second order multiscale differential operator wavelet transform $W_s^2 f(u)$, other characteristic points of the exemplary electrocardiogram signal f(t) are located (step 405). Specifically, the modulus maxima 33, 33' of the second order multiscale differential operator $W_s^2 f(u)$ respectively define the turning points 311, 311' of the first and second wave segments 31, 31'. Through the first and last modulus maxima 34, 34' of the third order multiscale differential operator $W_s^3 f(u)$ of the exemplary electrocardiogram signal f(t), the fade-away points 312, 312', which are usually difficult to determine in the prior art, of the first and second wave segments 31, 31' are located (step 406).

Figure 4:
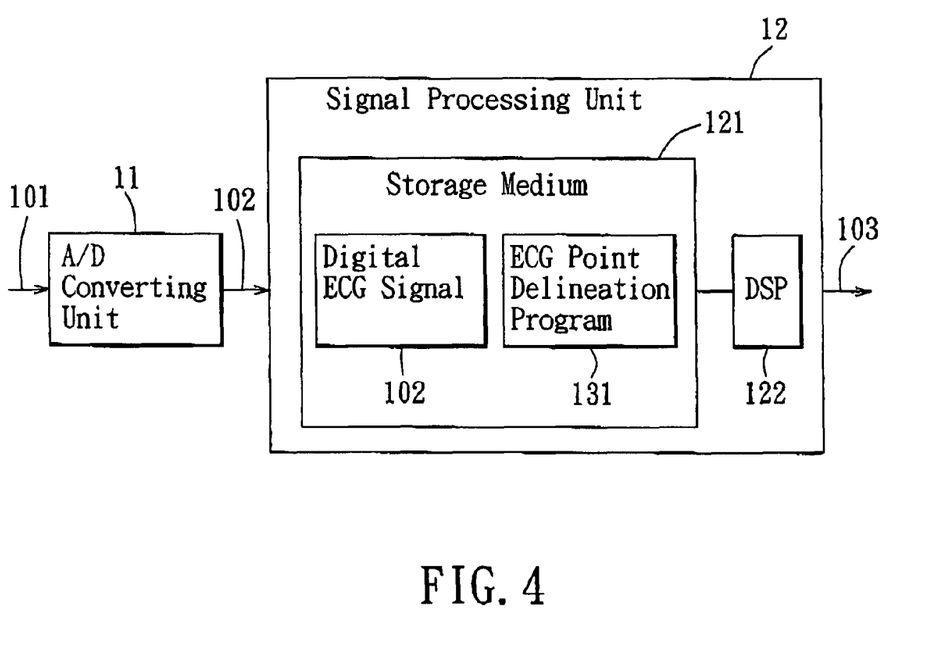
FIG. 4 is a block diagram of the preferred embodiment of an electrocardiogram signal analyzing system according to the present invention.

Referring now to FIG. 4, an electrocardiogram signal analyzing system 1 according to the preferred embodiment of the present invention includes an analog-to-digital (A/D) converter 11 and a signal processing unit 12. The signal processing unit 12 that is coupled electrically to the A/D converter 11, and includes a storage medium 121, and a digital signal processor 122 that is coupled electrically to the storage medium 121. The storage medium 121 has an electrocardiogram point delineation program 131 stored therein to implement the method for delineation of characteristic points in an electrocardiogram signal according to the present invention.

Figure 5:
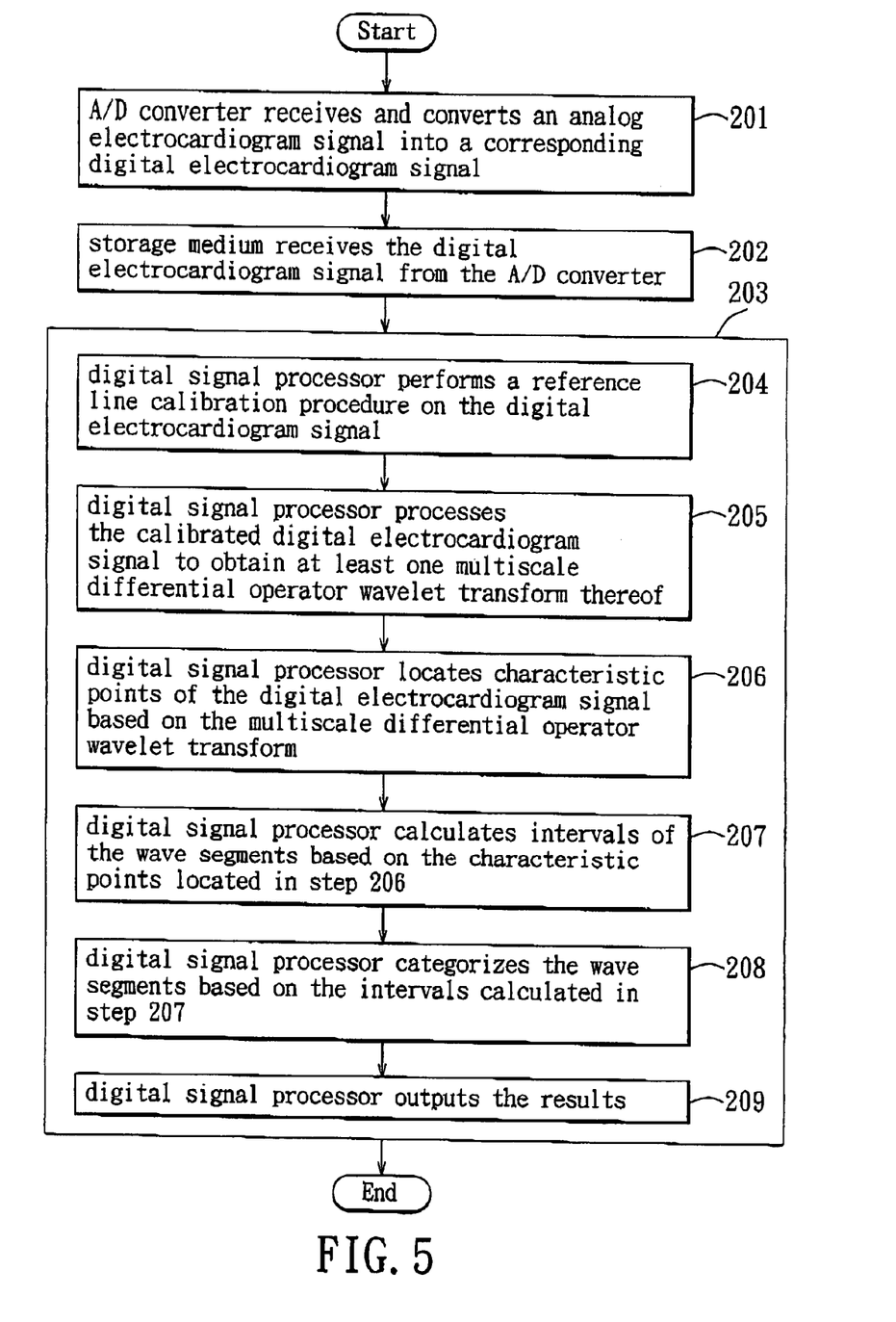
FIG. 5 is a flowchart to illustrate operation of the electrocardiogram signal analyzing system of FIG. 4.

With further reference to FIG. 5, the A/D converter 11 first receives an analog electrocardiogram signal 101 from an external source, and converts the analog electrocardiogram signal 101 into a corresponding digital electrocardiogram signal 102 (step 201). The storage medium 121 of the signal processing unit 12 then receives the digital electrocardiogram signal 102 from the A/D converter 11 (step 202). Subsequently, the digital signal processor 122 of the signal processing unit 12 retrieves the electrocardiogram point delineation program 131 from the storage medium 121, and performs consecutive steps of the method for delineation of characteristic points in the digital electrocardiogram signal 102 according to the present invention through execution of the electrocardiogram point delineation program 131 (step 203).

When executing the electrocardiogram point delineation program 131, the digital signal processor 122 first performs a reference line calibration procedure on the digital electrocardiogram signal 102 (step 204). The reference line calibration procedure is necessary because the respiratory cycles of the external source interfere with the analog electrocardiogram signal 101, resulting in shifting of the reference line of the analog electrocardiogram signal 101. The electrocardiogram point delineation program 131 involves means appropriate for reference line calibration procedure, such as a least square approximation calculation, or appropriate filters, etc.

Next, the digital signal processor 122 processes the calibrated digital electrocardiogram signal 102 to obtain at least one multiscale differential operator wavelet transform thereof (step 205). In this embodiment, a first order multiscale differential operator wavelet transform, a second order multiscale differential operator wavelet transform, and a third order multiscale differential operator wavelet transform are obtained in step 205.

Then, the digital signal processor 122 locates at least one characteristic point in at least one wave segment of the digital electrocardiogram signal 102 based on the at least one multiscale differential operator wavelet transform (step 206). In this embodiment, the digital signal processor 122 locates a P-wave peak point, a P-wave on point, a P-wave off point, a QRS-wave peak point, a QRS-wave on point, a QRS-wave off point, a T-wave peak point, a T-wave on point, and a T-wave off point in the digital electrocardiogram signal 102.

Based on the characteristic points located in step 206, the digital signal processor 122 further calculates intervals of the wave segments (step 207). In this embodiment, the intervals include a PR interval, a ST interval, a QT interval, a P-wave interval, a QRS-complex interval, and a T-wave interval.

Subsequently, based on the intervals calculated in step 207, the digital signal processor 122 categorizes the wave segments according to the morphology of the wave segments falling within corresponding intervals (step 208). In this embodiment, the T-wave segment is categorized into one of a positive/negative T-wave, an ascending/descending T-wave, and a biphasic T-wave.

Lastly, the digital signal processor 122 outputs the results 103 obtained through execution of the electrocardiogram point delineation program 131 (step 209).

Figure 6A:
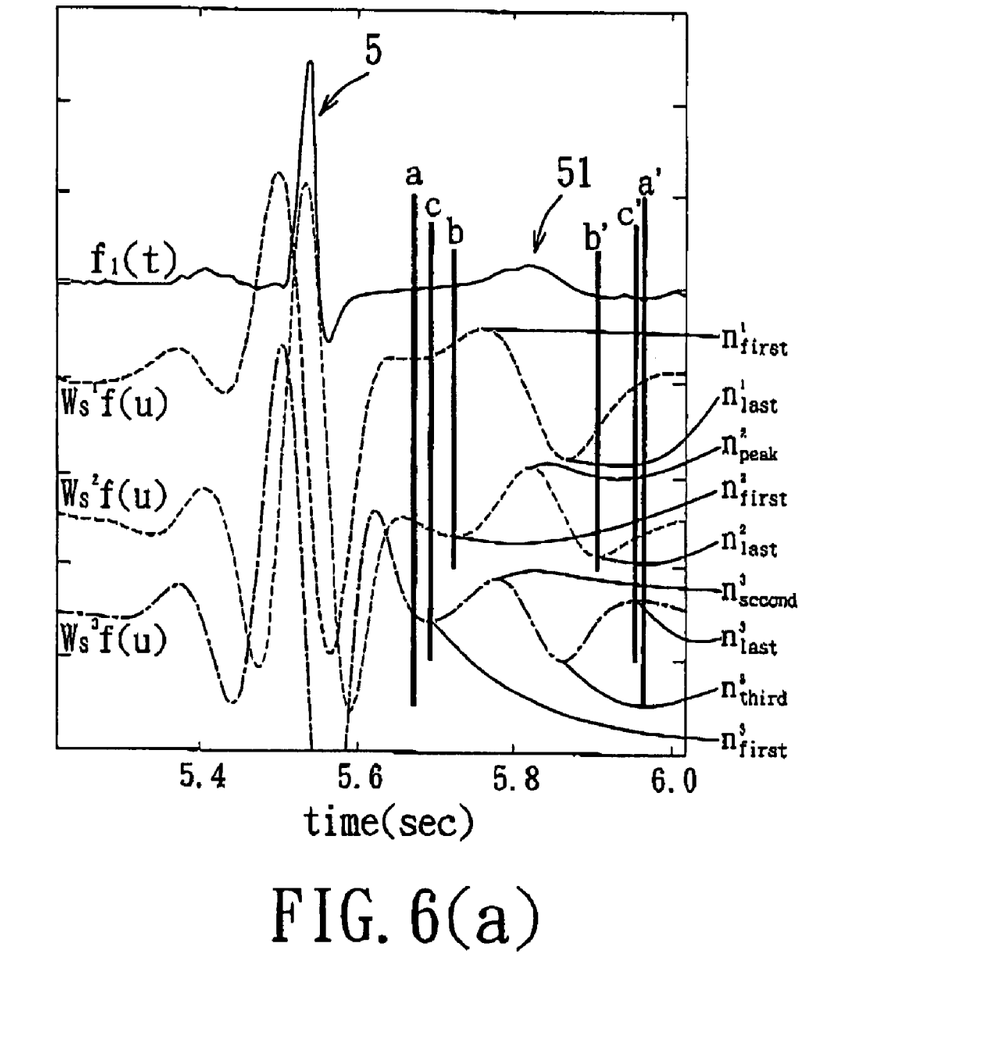

Shown in FIG. 6(a) is a first standard electrocardiogram signal $f_1(t)$ taken as an example for the digital electrocardiogram signal 102 for the purpose of illustration. A T-wave segment 51 of the first standard electrocardiogram signal $f_1(t)$ is selected to illustrate the results obtained through execution of the electrocardiogram point delineation program 131 in the above described manner for purposes of the following discussion.

Through execution of the electrocardiogram point delineation program 131, barriers (a), (a'), turning points (b), (b'), and fade-away points (c), (c') of the T-wave segment 51 in the first standard electrocardiogram signal $f_1(t)$ are located respectively by finding modulus maxima in the first, second and third order multiscale differential operator wavelet transforms $W_s^1 f(u)$, $W_s^2 f(u)$, $W_s^3 f(u)$ of the T-wave segment 51.

Specifically, two extremities of the first order multiscale differential operator wavelet transform $W_s^1 f(u)$ corresponding to the T-wave segment 51, i.e., a first modulus maximum $n_{first}^1$ and a last modulus maximum $n_{last}^1$, are determined. In an absolute value $|W_s^1 f(u)|$ of the first order multiscale differential operator wavelet transform $W_s^1 f(u)$, two local minima corresponding to the T-wave segment 51 are determined as the barriers (a), (a') of the T-wave segment 51. In addition, the zero-crossing of the first order multiscale differential operator wavelet transform $W_s^1 f(u)$ corresponding to the T-wave segment 51 defines the peak of the T-wave segment 51. Two extremities of the second order multiscale differential operator wavelet transform $W_s^2 f(u)$ corresponding to the T-wave segment 51, i.e., a first modulus maximum $n_{first}^2$ and a last modulus maximum $n_{last}^2$, are determined as the turning points (b), (b') of the T-wave segment 51. Two extremities of the third order multiscale differential operator wavelet transform $W_s^3 f(u)$ corresponding to the T-wave segment 51, i.e., a first modulus maximum $n_{first}^3$ and a last modulus maximum $n_{last}^3$, are determined as the fade-away points (c), (c') of the T-wave segment 51.

In determining the on and off points of the T-wave segment 51, the ratio of $|W_s^2 f(u)|$ to $|W_s^3 f(u)|$ is computed. If the ratio of $|W_s^2 f(u)|$ to $|W_s^3 f(u)|$ is larger than a proper parameter $\alpha$, the fade-away point (c) is selected as the T-wave on point, and the fade-away point (c') is selected as the T-wave off point. Otherwise, the turning points (b), (b') are selected respectively as the T-wave on point and the T-wave off point. In this embodiment, the proper parameter $\alpha$ is an empirical value of 0.26.

For this example, based on the modulus maxima in the different orders of multiscale differential operator wavelet transforms $W_s^1 f(u)$, $W_s^2 f(u)$, $W_s^3 f(u)$, the digital signal processor 122 categorizes the T-wave segment 51 into one of three categories, with the first category being positive/negative T-waves, the second category being ascending/descending T-waves, and the third category being biphasic T-waves.

Figure 6B:
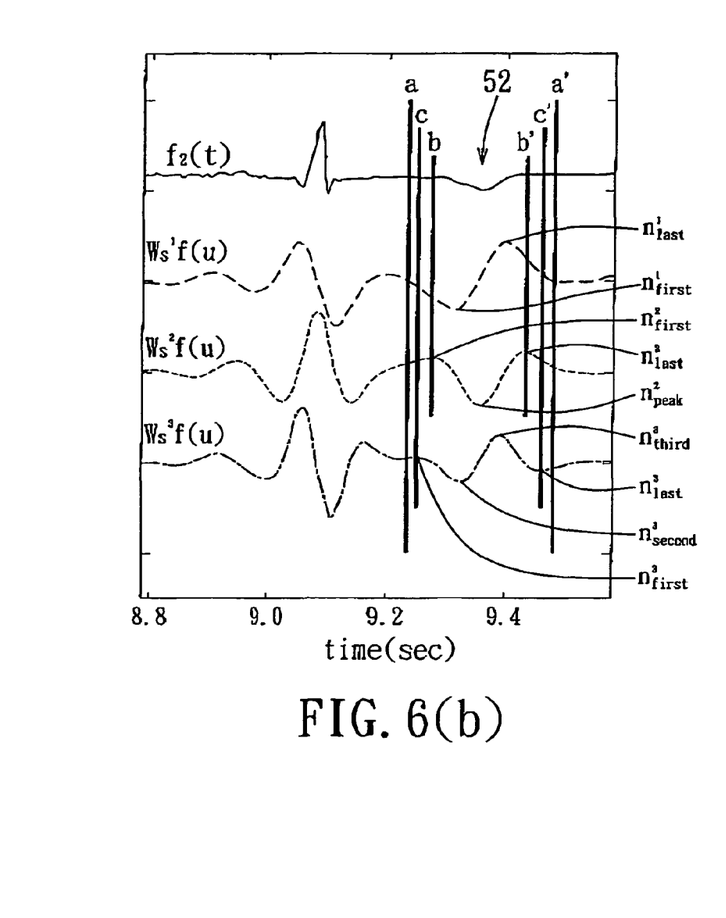

When there are two modulus maxima $n_{first}^1$ and $n_{last}^1$ in the first order multiscale differential operator wavelet transform $W_s^1 f(u)$, three modulus maxima $n_{first}^2$, $n_{peak}^2$ and $n_{last}^2$ in the second order multiscale differential operator wavelet transform $W_s^2 f(u)$, and four modulus maxima $n_{first}^3$, $n_{second}^3$, $n_{third}^3$ and $n_{last}^3$ in the third order multiscale differential operator wavelet transform $W_s^3 f(u)$ for a T-wave segment, the digital signal processor 122 categorizes the T-wave segment into the first category. For instance, the digital signal processor 122 categorizes the T-wave segment 51 of the first standard electrocardiogram signal $f_1(t)$ shown in FIG. 5(a), which is a positive T-wave, and the T-wave segment 52 of a second standard electrocardiogram signal $f_2(t)$ shown in FIG. 5(b), which is a negative T-wave, into the first category.

Figure 6C:
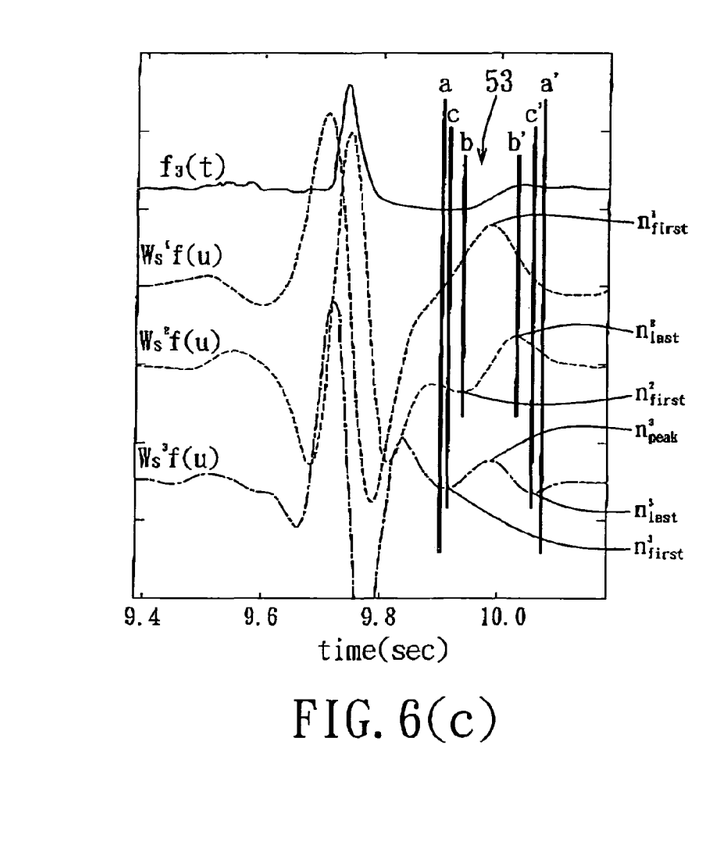
Figure 6D:
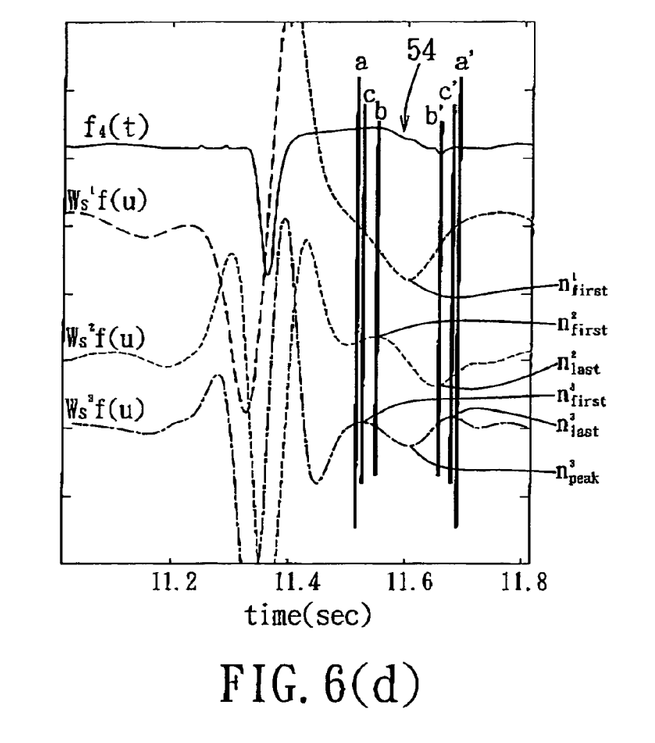

When there are a single modulus maximum $n_{first}^1$ in the first order multiscale differential operator wavelet transform $W_s^1 f(u)$, two modulus maxima $n_{first}^2$ and $n_{last}^2$ in the second order multiscale differential operator wavelet transform $W_s^2 f(u)$, and three modulus maxima $n_{first}^3$, $n_{peak}^3$ and $n_{last}^3$ in the third order multiscale differential operator wavelet transform $W_s^3 f(u)$ for a T-wave segment, the digital signal processor 122 categorizes the T-wave segment into the second category. For instance, the digital signal processor 122 categorizes the T-wave segment 53 of a third standard electrocardiogram signal $f_3(t)$ shown in FIG. 5(c), which is an ascending T-wave, and the T-wave segment 54 of a fourth standard electrocardiogram signal $f_4(t)$ shown in FIG. 5(d), which is a descending T-wave, into the second category.

Figure 6E:
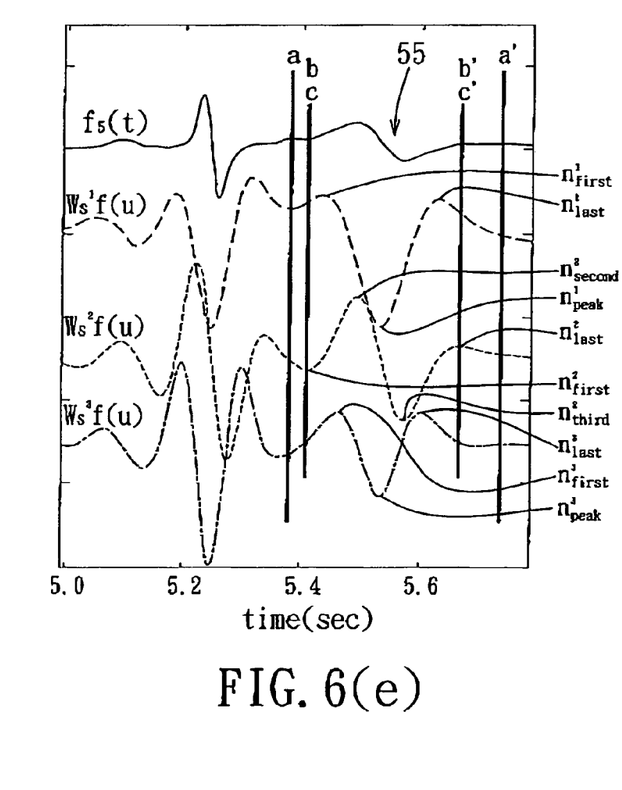

When there are three modulus maxima $n_{first}^1$, $n_{peak}^1$ and $n_{last}^1$ in the first order multiscale differential operator wavelet transform $W_s^1 f(u)$, four modulus maxima $n_{first}^2$, $n_{second}^2$, $n_{third}^2$ and $n_{last}^2$ in the second order multiscale differential operator wavelet transform $W_s^2 f(u)$, and three modulus maxima $n_{first}^3$, $n_{peak}^3$ and $n_{last}^3$ in the third order multiscale differential operator wavelet transform $W_s^3 f(u)$ for a T-wave segment, the digital signal processor 122 categorizes the T-wave segment in the third category. For instance, the digital signal processor 122 categorizes the T-wave segment 53 of a fifth standard electrocardiogram signal $f_5(t)$ shown in FIG. 5(e), which is a biphasic T-wave, into the third category.

To evaluate and validate the present invention, several conventional methods, such as wavelet-based delineator (WBD), low-pass-differentiator-based method (LPD), and T-U complex detector method (TU), were conducted on electrocardiogram signals recorded in a QT database (QTDB), and the results of which were used to compare with the results obtained using the method according to the present invention, which incorporates multiscale differential operator (MDO) calculations. The results obtained for the conventional methods and the method according to the present invention (denoted by MDO) are tabulated in Table 1 below, where "#" represents the total number of heart beats measured. In addition, the T-wave on point, the T-wave peak point, and the T-wave off point are measured in milliseconds and are expressed as "M±SD", where "M" represents average mean and "SD" represents average standard deviation.

TABLE 1

|  | WBD | LPD | TU | MDO |
| --- | --- | --- | --- | --- |
| T-wave on point | Not reported | Not reported | 20.9 ± 29.6 | −7.9 ± 11.3 |
| # | Not reported | Not reported | 1399 | 1341 |
| T-wave peak point | 0.2 ± 13.9 | −7.2 ± 14.3 | −12.0 ± 23.4 | −0.9 ± 13.1 |
| # | 3542 | 3542 | 3528 | 3542 |
| T-wave off point | −1.6 ± 18.1 | 13.5 ± 27.0 | 0.8 ± 30.3 | −1.8 ± 16.1 |
| # | 3542 | 3542 | 3528 | 3542 |

It can be seen from Table 1 that the method according the present invention resulted in the smallest average standard deviation for all measurements in the delineation of characteristic points of the T-waves (i.e., the T-wave on point, the T-wave peak point, and the T-wave off point), and therefore demonstrates the best delineation effect and accuracy.

In sum, the present invention integrates wavelet transform and multiscale differential operator to accurately locate characteristic points of an electrocardiogram signal so as to delineate the wave segments in the electrocardiogram signal. The present invention is even capable of delineating T-wave segments, whose on points are normally difficult to detect using conventional methods, with high accuracy.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for delineation of characteristic points in an electrocardiogram signal, comprising the step of:
   (a) processing the electrocardiogram signal to obtain a first order multiscale differential operator wavelet transform, a second order multiscale differential operator wavelet transform, and a third order multiscale differential operator wavelet transform thereof; and
   (b) locating at least one characteristic point in at least one wave segment of the electrocardiogram signal based on the first order multiscale differential operator wavelet transform, the second order multiscale differential operator wavelet transform, and the third order multiscale differential operator wavelet transform, said at least one characteristic point being at least one of a P-wave peak point, a P-wave on point, a P-wave off point, a QRS-wave peak point, a QRS-wave on point, a QRS-wave off point, a T-wave peak point, a T-wave on point, and a T-wave off point.

2. The method as claimed in claim 1, wherein, in step (b), two characteristic points of the wave segment are located, and include an on point and an off point of the wave segment, the method further comprising the step of:
   (c) calculating an interval based on the on point and the off point thus located.

3. The method as claimed in claim 2, wherein the interval is one of a PR interval, a ST interval, a QT interval, a P-wave interval, a QRS-complex interval, and a T-wave interval.

4. The method as claimed in claim 1, wherein, in step (b), three characteristic points of the wave segment are located, and include an on point, a peak point, and an off point of the wave segment, the method further comprising the steps of:
   (c) calculating an interval based on the on point and the off point thus located; and
   (d) categorizing the wave segment according to morphology of the wave segment falling within the interval.

5. The method as claimed in claim 4, wherein, in step (d), the wave segment is categorized into one of a positive/negative T-wave, an ascending/descending T-wave, and a biphasic T-wave.

6. A non-transitory computer-readable storage medium comprising program instructions for causing a computing apparatus to execute consecutive steps of a method for delineation of characteristic points in an electrocardiogram signal, said method comprising:
   (a) receiving an electrocardiogram signal;
   (b) processing the electrocardiogram signal to obtain a first order multiscale differential operator wavelet transform, a second order multiscale differential operator wavelet transform, and a third order multiscale differential operator wavelet transform; and
   (c) locating at least one characteristic point in at least one wave segment of the electrocardiogram signal based on the first order multiscale differential operator wavelet transform, the second order multiscale differential operator wavelet transform, and the third order multiscale differential operator wavelet transform, said at least one characteristic point being at least one of a P-wave peak point, a P-wave on point, a P-wave off point, a QRS-wave peak point, a QRS-wave on point, a QRS-wave off point, a T-wave peak point, a T-wave on point, and a T-wave off point.

7. An electronic device comprising program instructions for causing said electronic device to execute consecutive steps of a method for delineation of characteristic points in an electrocardiogram signal, said method comprising:
   (a receiving an electrocardiogram signal;
   (b) processing the electrocardiogram signal to obtain a first order multiscale differential operator wavelet transform, a second order multiscale differential operator wavelet transform, and a third order multiscale differential operator wavelet transform thereof; and
   (c) locating at least one characteristic point in at least one wave segment of the electrocardiogram signal based the first order multiscale differential operator wavelet transform, the second order multiscale differential operator wavelet transform, and the third order multiscale differential operator wavelet transform, said at least one characteristic point being at least one of a P-wave peak point, a P-wave on point, a P-wave off point, a QRS-wave peak point, a QRS-wave on point, a QRS-wave off point, a T-wave peak point, a T-wave on point, and a T-wave off point.

8. An electronic device capable of delineating characteristic points in an electrocardiogram signal, comprising:
   means for receiving an electrocardiogram signal;
   means for processing the electrocardiogram signal to obtain a first order multiscale differential operator wavelet transform, a second order multiscale differential operator wavelet transform, and a third order multiscale differential operator wavelet transform thereof; and
   means for locating at least one characteristic point in at least one wave segment of the electrocardiogram signal based on the first order multiscale differential operator wavelet transform, the second order multiscale differential operator wavelet transform, and the third order multiscale differential operator wavelet transform, said at least one characteristic point being at least one of a P-wave peak point, a P-wave on point, a P-wave off point, a QRS-wave peak point, a QRS-wave on point, a QRS-wave off point, a T-wave peak point, a T-wave on point, and a T-wave off point.

9. An electrocardiogram signal analyzing system, comprising:
   an analog-to-digital converting unit for converting an analog electrocardiogram signal into a corresponding digital electrocardiogram signal; and
   a signal processing unit coupled electrically to said analog-to-digital converting unit and including
   a non-transitory storage medium for receiving and storing the digital electrocardiogram signal, and having an electrocardiogram point delineation program stored therein, and
   a digital signal processor coupled electrically to said non-transitory storage medium for retrieving the electrocardiogram point delineation program, and for performing consecutive steps of a method for delineation of characteristic points in the digital electrocardiogram signal through execution of the electrocardiogram point delineation program, the method including: (a) processing the digital electrocardiogram signal to obtain a first order multiscale differential operator wavelet transform, a second order multiscale differential operator wavelet transform and a third order multiscale differential operator wavelet transform thereof; and (b) locating at least one characteristic point in at least one wave segment of the electrocardiogram signal based on the first order multiscale differential operator wavelet transform, the second order multiscale differential operator wavelet transform, and the third order multiscale differential operator wavelet transform, said at least one characteristic point being at least one of a P-wave peak point, a P-wave on point, a P-wave off point, a QRS-wave peak point, a QRS-wave on point, a QRS-wave off point, a T-wave peak point, a T-wave on point, and a T-wave off point.

10. The electrocardiogram signal analyzing system as claimed in claim 9, wherein, in step (b) of the method, two characteristic points of the wave segment are located, and include an on point and an off point of the wave segment, the method further comprising the step of:
(c) calculating an interval based on the on point and the off point thus located.

11. The electrocardiogram signal analyzing system as claimed in claim 10, wherein the interval is one of a PR interval, a ST interval, a QT interval, a P-wave interval, a QRS-complex interval, and a T-wave interval.

12. The electrocardiogram signal analyzing system as claimed in claim 9, wherein, in step (b) of the method, three characteristic points of the wave segment are located, and include an on point, a peak point, and an off point of the wave segment, the method further comprising the steps of:
(c) calculating an interval based on the on point and the off point thus located; and
(d) categorizing the wave segment according to morphology of the wave segment falling within the interval.

13. The electrocardiogram signal analyzing system as claimed in claim 12, wherein, in step (d) of the method, the wave segment is categorized into one of a positive/negative T-wave, an ascending/descending T-wave, and a biphasic T-wave.

14. The method as claimed in claim 1, wherein the first order multiscale differential operator wavelet transform, the second order multiscale differential operator wavelet transform and the third order multiscale differential operator wavelet transform are obtained in step (a) according to the equation of $$W_s^n f(u) = s^n \frac{d^n}{du^n} (f \otimes \overline{\theta}_s)(u), \text{ where } \overline{\theta}_s(t) = s^{\frac{-1}{2}} \theta * \left(\frac{-t}{s}\right),$$

in which $W_s^n f(u)$ with n=1, n=2 and n=3 respectively denote the first, second and third order multiscale differential operator wavelet transforms, u denotes a translation, s denotes a scale of a mother wavelet function ψ(t) for decomposing the electrocardiogram signal represented by f(t) into a plurality of elementary elements.

15. The method as claimed in claim 3, wherein in determining the T-wave on point and the T-wave off point, step (b) includes the sub-steps of:
(b-1) finding a first modulus maximum and a last modulus maximum of the second order multiscale differential operator wavelet transform corresponding to a T-wave segment, and designating the first and last modulus maxima respectively as turning points of the T-wave segment;
(c-2) finding a first modulus maximum and a last modulus maximum of the third order multiscale differential operator wavelet transform corresponding to the T-wave segment, and designating the first and last modulus maxima respectively as fade-away points of the T-wave segment;
(c-3) computing a ratio of the absolute value of the second order multiscale differential operator to the absolute value of the third order multiscale differential operator; and
(c-4) determining that the fade-away points are respectivly the T-wave on and off points if the ratio is larger than a predetermined parameter, and determining that the turning points are respectively the T-wave on and off points when otherwise.

\* \* \* \* \*

UNITED STATES PATENT AND TRADEMARK OFFICE
CERTIFICATE OF CORRECTION

PATENT NO. : 8,285,369 B2
APPLICATION NO. : 11/807800
DATED : October 9, 2012
INVENTOR(S) : Cheng-Deng Kuo et al.

It is certified that error appears in the above-identified patent and that said Letters Patent is hereby corrected as shown below:

Title Page, item (73), Assignee: After "Hospital" insert --, VAC--.

Signed and Sealed this
Twenty-sixth Day of February, 2013

Teresa Stanek Rea
*Acting Director of the United States Patent and Trademark Office*